Nov. 12, 1957 H. T. SANDERS Plant Pat. 1,659
ROSE PLANT
Filed March 14, 1957
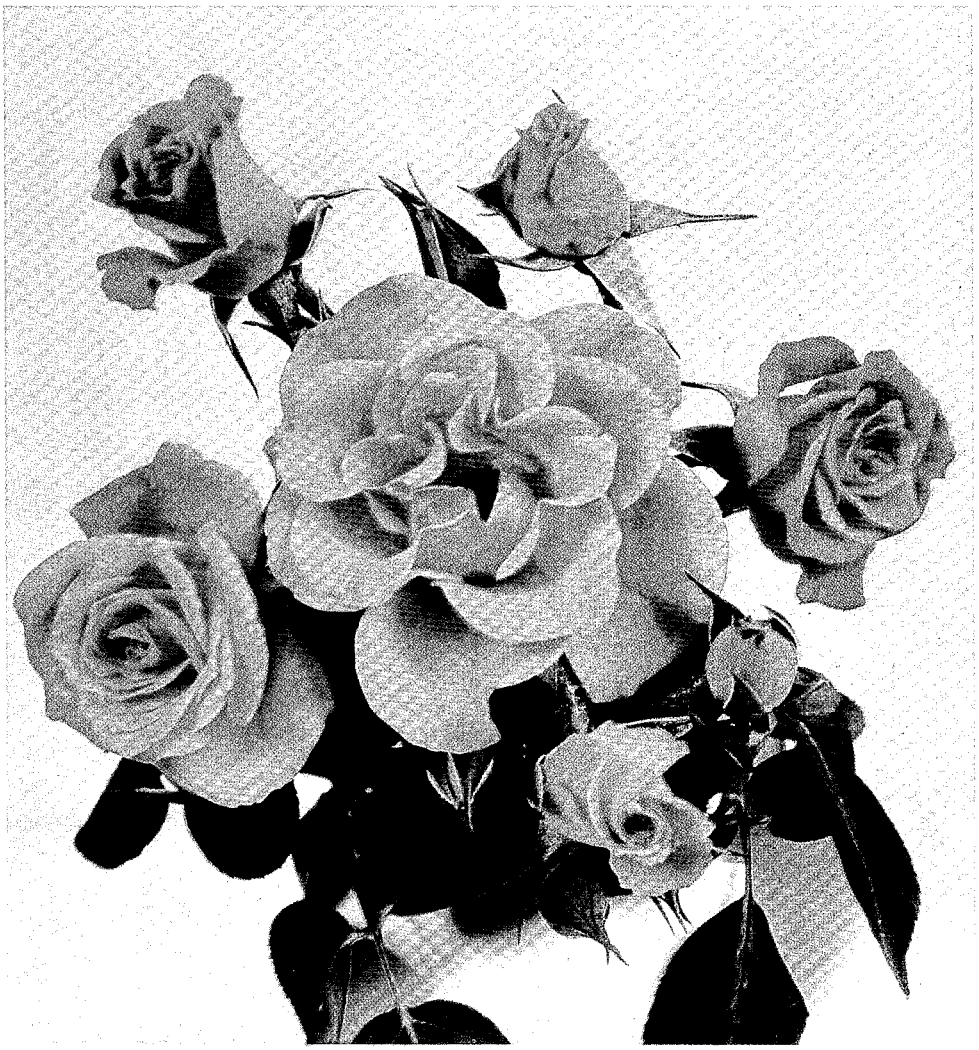
INVENTOR
H. T. Sanders
BY Robb & Robb
ATTORNEYS United States Patent Office Plant Pat. 1,659
Patented Nov. 12, 1957

1,659

ROSE PLANT

Harold T. Sanders, Tyler, Tex.

Application March 14, 1957, Serial No. 646,183
1 Claim. (Cl. 47—61)

The present invention relates to a new and distinct variety of rose plant of the floribunda class, which was discovered by me as a sport of the variety "Red Ripples" (unpatented).

The new variety was discovered by me in a field block of "Red Ripples" being grown on cultivated property leased by me and under my complete control and supervision, near Tyler, Texas.

At the time of the discovery, my attention was initially attracted to a particular plant of "Red Ripples" in the field block aforementioned by virtue of the fact that the plant exhibited a more vigorous growth than the normal growth of the parent variety, and by the additional fact that it bore Pink flowers, as distinguished from the normally Red flowers of the parent variety. Upon closer observation, I found that the plant to which my attention had been attracted had sported, and I thereupon took steps to preserve the same, keep it under observation, and to later asexually reproduce the sport. These observations and asexual reproductions, as performed by me by budding, near Tyler, Texas, conclusively established that the vigorous growth and the distinctive Pink flower color of the sport were fixed and capable of being transmitted through succeeding propagations, along with other improved characteristics which I found to be present in the new sport, and which altogether represent a unique combination of features in a rose variety of this class. The most outstanding characteristics of the new variety are enumerated as follows:

(1) More vigorous growth;

(2) Almost a complete absence of prickles on the branches, as compared with the usual prickles between the thorns on the branches of "Red Ripples";

(3) A more prolific blooming habit and a more prolonged blooming period, even under extremely hot and dry weather conditions, as compared with "Red Ripples";

(4) Good self-cleaning habit of the plant as the blooms mature; and (5) The distinctive and unfading Pink general color tonality of the blooms.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology of the flowers in accordance with the "Flower Color Detector Chart" published by American Horticultural Council, Inc., and with other color terminology given in accordance with general color terms of ordinary dictionary significance:

Parentage: Sport of "Red Ripples."
Type: Hardy; bush.
Class: Floribunda.
Propagation: Holds its distinguishing characteristics through succeeding propagations by budding.

*Flower*

(Observations made from specimens grown in a field near Tyler, Texas.)

Continuity: Continuous.
Fragrance: Moderate. Nature—tea.
Flowers borne: Several to stem; in rounded clusters; on stems of medium length.
Quantity of bloom: Abundant, outdoors.
Bud:
*Peduncle.*—Medium length; medium caliper; medium erect; medium smoothness; with numerous Green prickles. Color—Medium Green.
*Before calyx breaks.*—Size—medium. Form—oval; without foliaceous appendages on the surface of the bud; with slender foliaceous sepals extending beyond the tip of the bud equal to approximately ¼ of its length. Color—Light Green.
*As calyx breaks.*—Color—from Light to Strong Purplish Red.
*As first petal opens.*—Size—medium. Form—ovoid. Color: outside—from Light to Strong Purplish Red; inside—from Light to Strong Purplish Red.
*Opening.*—Opens up well.
Bloom:
*Size (when fully open).*—Medium; from 2 to 2½ inches.
*Petalage.*—Very double; from 18 to 24 petals; arranged irregularly.
*Form.*—High-centered at first and remaining high-centered; petals being at first loosely rolled outward, and becoming very loosely rolled outward later at maturity.
Petals:
*Texture.*—Medium thin; soft.
*Appearance.*—Inside—satiny. Outside—satiny.
*Shape.*—Outside—obovate. Intermediate—obovate. Inside—obovate.

This description of a newly opened flower was made from a rose grown outdoors in the month of October, near Tyler, Texas.

*Color.*—Outer petal: outside surface—from Light to Strong Purplish Red; inside surface—from Light to Strong Purplish Red. Intermediate petal: outside surface—from Light to Strong Purplish Red; inside surface—from Light to Strong Purplish Red. Inner petal: outside surface—from Light to Strong Purplish Red; inside surface—from Light to Strong Purplish Red.

This description was made from a rose that was open for three days outdoors in the month of October, near Tyler, Texas:

*Color.*—Outer petal: outside surface—from Light to Strong Purplish Red; inside surface—from Light to Strong Purplish Red. Inner petal: outside surface—from Light to Strong Purplish Red; inside surface—from Light to Strong Purplish Red.
*General color effect.*—Newly opened flower—from Light to Strong Purplish Red. Three days open—from Light to Strong Purplish Red.
*Behavior.*—Drop off cleanly; constant solid color is main trait.
*Flower longevity.*—On bush in garden—5 days in October. Cut roses grown outdoors and kept at living room temperatures—5 days in October.

*Reproductive organs*

Stamens: Medium number; irregularly arranged around pistils. Color—Yellow.

Filaments: Medium length; most with anthers. Color—reddish.
Anthers: Medium size. Color—Yellow.
Pollen: Moderate abundance. Color—Yellow.
Pistils: Medium number.
Styles: Even; medium length; medium caliper; columnar.
Stigma: Color—Yellow.
Ovaries: All enclosed in calyx.
Hips: Globular; moderately smooth; walls thin. Color—Green.
Sepals: Permanent; moderate length; straight. Color—Light Green.
Seeds: Very few; medium size.

*Plant*

Foliage:

*Leaves.*—Compound of 5 to 7 leaflets; normal abundance; moderately small size; heavy.

*Leaflets.* — Shape — oval. Apex — acute. Base—acute. Margin—simply serrate.

*Color.*—Mature: upper surface—Normal Green; under surface—Light Green. Young: upper surface—Normal Green; under surface—Light Green.

*Rachis (the supporting stem of the compound leaf).*—Medium caliper. Upper side—smooth. Under side—moderately prickly.

*Stipules.*—Moderately short; medium width; with short points turning out at an angle of more than 45°.

Disease resistance: Similar to that of the variety "Red Ripples," as compared with this parent by growing under comparable cultural conditions near Tyler, Texas.

Growth:

*Habit.*—Bushy; upright; much-branched.

*Growth.*—Vigorous.

*Canes.*—Medium caliper.

*Main stems.*—Color—Dull Green. Thorns—few; short; hooked downward; with long, narrow base. Prickles—few; color—Brown. Hairs—none.

*Branches.* — Color — Dull Green. Thorns — few; short; hooked downward; with long, narrow base. Prickles—few; color—Brown. Hairs—none.

*New shoots.*—Color—Green. Thorns—few; short; hooked downward; with narrow base. Prickles—few; color—Brown. Hairs—none.

I claim:

A new and distinct variety of rose plant of the floribunda class, substantially as herein shown and described, characterized particularly as to novelty by its more vigorous growth, the relatively few prickles on its branches, its more prolific blooming habit and more prolonged blooming period even under extremely hot and dry weather conditions, the good self-cleaning habit of the plant as the blooms mature, and the distinctive and unfading Pink general color tonality of its blooms, all as compared with the variety "Red Ripples" (unpatented).

No references cited.